(12) United States Patent
Mason et al.

(10) Patent No.: US 6,342,522 B1
(45) Date of Patent: Jan. 29, 2002

(54) MICROBIOCIDAL COMPOSITIONS

(76) Inventors: George William Mason, Sutton Road, R D 4; Peter James Hayward, Plymouth Road, R D 4; Wallace J Rae, 8 Mahoe Street; John Doyle, 35 Ngaio Street, all of New Plymouth (NZ)

( * ) Notice: Subject to any disclaimer, the term of this patent is extended or adjusted under 35 U.S.C. 154(b) by 0 days.

(21) Appl. No.: 09/649,135

(22) Filed: Aug. 28, 2000

Related U.S. Application Data

(63) Continuation of application No. 09/298,168, filed on Apr. 23, 1999, now abandoned.

(30) Foreign Application Priority Data

Apr. 24, 1998 (NZ) .................................................. 330286

(51) Int. Cl.$^7$ ........................ A01N 47/10; A01N 37/30; A01N 37/52
(52) U.S. Cl. ........................ 514/479; 514/478; 514/554; 514/634; 514/635
(58) Field of Search ................................ 574/478, 479, 574/554, 634, 635

(56) References Cited

U.S. PATENT DOCUMENTS

| | | | |
|---|---|---|---|
| 4,452,805 A | | 6/1984 | Hayes .................... 424/273 R |
| 5,126,360 A | | 6/1992 | Dutzmann et al. .......... 514/383 |
| 5,219,875 A | * | 6/1993 | Sherba et al. ................ 514/373 |
| 5,385,926 A | * | 1/1995 | Ludwig et al. ............. 514/383 |

OTHER PUBLICATIONS

Clive Tomlin, "The Pesticide Manual—Incorporating The Agrochemicals Handbook", Tenth Edition, pp. 382–384, 545–547, 593–594, 855–856, 1248.

* cited by examiner

*Primary Examiner*—Allen J. Robinson
(74) *Attorney, Agent, or Firm*—Yougn & Thompson

(57) ABSTRACT

A microbiocidal composition including a first component comprises a guanidine compound, a second component which comprises either prochloraz, propiconazole or iodocarb, wherein the weight ratio of first component to second component is in the range of from about 32:1 to about 1:16.

The microbiocidal composition provides effective and broader control of micro-organisms in various industrial systems and for household products, agricultural products and biomedical products.

10 Claims, No Drawings

MICROBIOCIDAL COMPOSITIONS

CROSS-REFERENCE TO RELATED APPLICATIONS

This application is a continuation of application Ser. No. 09/298,168, filed Apr. 23, 1999, and now abandoned.

BACKGROUND OF THE INVENTION

This invention concerns microbiocidal compositions and more particularly microbiocidal compositions which are intended to provide more effective and broader control of micro-organisms in various industrial systems and for household products, agricultural products, and biomedical products etc.

In particular the present invention relates to the use of a composition of 1-dodecylguanidinium acetate, hereafter referred to as "dodine" or a mixture of aminated amines, the main component being 1,1-iminodi(octamethylene) diguanidine, hereafter referred to as "guazatine" or iminoctadine triacetate, hereafter referred to as "Befran", with one or more of the following compounds: a triazole derived fungicide, an example being 1-(2-(2,4-dichlorophenyl)-4-propyl-1-1,3-dioxolan-2-ylmethyl)-1H-1,2,4-triazole, hereafter referred to as "propiconazole"; a carbamoyl imidazole compound, an example being N-propyl-N-(2-(2,4,6-trichlorophenoxy)ethyl)-imidazole-1-carboximide, hereafter referred to as "prochloraz"; a iodine containing compound, an example being 3-iodo-2-propynylbutyl carbamate, hereafter referred to as "iodocarb".

The term "microbiocidal" (or "antimicrobiocidal" or "biocidal") as Used herein is intended to encompass, but is not restricted to all fungi and bacteria causing rot, mildew, stain or mould.

SUMMARY OF THE INVENTION

It is an object of this invention to provide synergistic compositions which overcome disadvantages of known microbiocidal compositions.

We have found that compositions formed from guanidine type compounds and one or more of the specified secondary compounds erochloraz, propiconazole or iodocarb unexpectedly afford synergistic antimicrobial activity against a wide range of microorganisms: the disruptive action on the organisms by the two compounds together is unexpectedly greater than the sum of both compounds taken alone. This synergy does not arise from the expected activity of the components nor from the expected improvement in activity As a result of the synergy, the effective dose required can be lowered, which is not only more economical but also increases safety margins.

The synergistic compositions of the present invention provide more effective and broader control of microorganisms in a number of systems.

The present invention thus provides a composition having microbiocidal activity which includes dodine, guazatine or Befran and a second component selected from one or more of the group consisting of propiconazole, iodocarb, prochloraz and other known chemicals with funcidial activity; wherein the weight ratio of dodine, guazatine or Befran to the second component is from about 150:1 to 1:250.

According to one broad aspect of the invention there is provided microbiocidal composition including a first component comprises a guanidine compound, a second component which comprises either prochloraz, propiconazole or iodocarb, wherein the weight ratio of first component to second component is in the range of from about 32:1 to about 1:16.

Preferably the guanidine compound is guazatine, dodine or Befran.

According to a second broad aspect of the invention there is provided a microbiocidal product containing from about 5 to about 30% of the composition of the preceding broad aspect.

In a preferred form the microbiocidal product contains an emulsifier and water.

According to a further broad aspect there is provided a method for inhibiting the growth of fungi, particularly wood destroying fungi or wood staining or moulding fungi in or on a locus subject to contamination by bacteria, fungi, or algae, which comprises incorporating onto or into the locus, an amount of the composition of the first broad aspect which is effective to effect adversely the growth of the fungi.

The locus can be an aqueous medium, and the composition additionally contains an emulsifier and water.

Preferably the weight ratio of first component to second component is in the range of from about 32:1 to about 1:2.

DESCRIPTION OF THE PREFERRED EMBODIMENTS

Applications of the synergistic antimicrobial compositions of the present invention include but are not limited to inhibiting the growth of bacteria and fungi in aqueous paints and coatings, adhesives, sealants, latex emulsions, and joint cements; preserving cutting fluids, controlling slime-producing bacteria and fungi in pulp and paper mills and cooling towers; as a spray or dip treatment for textiles and leather to prevent mould growth, protecting paint films, especially exterior paints, from attack by fungi which occurs, during weathering of the paint film; preventing bacterial and fungal growth in paper coatings and coating processes; controlling bacterial and fungal growth and deposits during the manufacture of various specialty boards, eg cardboard, fibre board, plywood, oriented strand board, laminated veneer lumber, laminated lumber and particle board; preventing sap stain discolouration on freshly cut wood of various kinds; preventing rot and other fungal degrade on and in dry cut wood of various kinds; inhibiting the growth; inhibiting the growth of harmful bacteria, yeasts, fungi on plants, trees, fruits, seeds, or soil; preserving agricultural formulations, and the like.

The compositions of the invention may be added separately to any system or may be formulated as a simple mixture comprising its essential ingredients, and if desired a suitable carrier or solvent, or an aqueous emulsion or dispersion.

The invention also provides a method of inhibiting the growth of fungi, in a locus subject to contamination by fungi, which comprises incorporating into or onto the locus in an amount which is affective to adversely affect the growth of fungi any of the compositions defined above.

The composition of the invention can be formulated as a solution in a wide range of organic solvents. The solutions generally contain about 5 to 60% by weight of the active composition. It is generally more convenient to provide the compositions in a water-diluted form; this may be accomplished by adding emulsifier to the organic solution followed by dilution with water.

In general, the weight ratio of the guanidine type compound to the second component in the composition may be in the range of from about 150:1 to about 1:250. Other specific and preferred ratios are given in the examples.

The synergism of two-component compositions is demonstrated by testing a wide range of concentrations and ratios of compounds, generated by two-fold serial dilutions in a Malt Agar (Gibco) growth medium of a microbicide in one dimension and another microcide in the second dimensions, against fungi Coriolus versicolor, Tyromyces palustris, Alternaria sp, Ophiostoma sp., Diplodia sp., or Penicillium sp. Each test tube was inoculated to make about $5 \times 10^5$ fungi per mil. The lowest concentrations of each compound or mixtures to inhibit visible growth (turbidity) at 30° C. for the fungi for 7 days were taken as the minimum inhibitory concentration (MIC). The MIC were taken as end points of activity. End points for the mixtures of compound A (Guanadine component) and Compound B (second Component microbiocide) were then compared with the end points for the guanadine component A alone and compound B alone. Synergism was determined by a commonly used and accepted method described by Kull, F. C.; Eisman, P. C.; Sylwestrowicz, H. D. and Mayer, R. L. in Applied Microbiology 9:538–541 (1961) using the ratio determined by Qa/QA+Qb/QB==Synergy Index (SI) wherein:

QA=concentration of compound A in parts per million (ppm), acting alone, which produced an end point.

Qa=concentration of compound A in ppm, in the mixture which produced an end point.

QB=concentration of compound B in ppm, acting alone which produced an end point.

Qb=concentration of compound B in ppm, in the mixture which produced an end point.

When the sum of Qa/QA and Qb/QB is greater than one, antagonism is indicated. When the sum is equal to one additivity is indicated, and when less than one synergism is demonstrated.

The test results for demonstration of synergism of microbicide combinations are shown in Tables 1 to 4. Each table concerns the combination of the guanidine component and one other secondary compound . . . , and shows:

1. the identity of the second microbicide (Compound B).
2. test against Coriolus versicolor, Tyromyces palustris, Alternaria sp, Ophiostoma sp., Diplodia .sp., or Penicillium sp.
3. the end-point activity in ppm measured by MIC for compound A alone (QA), for compound B alone (QB) for compound A in the mixture(Qa) or for compound P in the mixture (Qb).
4. the calculation of synergy index (SI) based on the formula the guanidine compound (compound A) to Compound B. in the particular combination (A:B).
5. the range of weight ratios for synergism and the preferred weight ratios. It will be appreciated by those skilled in the art that the ratios given are approximate only.

The MIC values of each compound tested alone (QA or QB) are end-point activities except where the value is expressed as x0.10. In these cases, the end-point activity was not seen at the highest tested concentration. For purpose of calculation of the synergy index and for operational definition of MIC, the reported value could be an underestimate of the true MIC; thus the true synergy index could be even lower.

TABLE 1

Compound A = Guazatine
Compound B = Prochloraz

| ORGANISM | QA | QB | Qa | Qb | Qa/QA | Qb/QB | SI | A:B |
|---|---|---|---|---|---|---|---|---|
| c versicolor | 32 | 4 | 6 | 2 | 0.19 | 0.50 | 0.69 | 3:1 |
| T palustri | 128 | 64 | 48 | 16 | 0.38 | 0.25 | 0.63 | 3:1 |
|  | 128 | 64 | 16 | 48 | 0.13 | 0.75 | 0.88 | 1:3 |
|  | 128 | 128 | 64 | 64 | 0.50 | 0.50 | 1.00 | 1:1 |
| Alternaria sp | 32 | 4 | 0.75 | 0.25 | 0.02 | 0.06 | 0.09 | 3:1 |
|  | 32 | 4 | 0.25 | 0.75 | 0.01 | 0.19 | 0.20 | 1:3 |
| Ophiosroma sp | 1 | 2 | 0.75 | 0.25 | 0.75 | 0.13 | 0.88 | 3:1 |
|  | 1 | 2 | 0.25 | 0.75 | 0.25 | 0.38 | 0.63 | 1:3 |
| Diplodia sp | 64 | 4 | 1.5 | 0.50 | 0.02 | 0.13 | 0.15 | 3:1 |
|  | 64 | 4 | 0.50 | 1.50 | 0.01 | 0.38 | 0.38 | 1:3 |
|  | 64 | 16 | 8 | 8 | 0.13 | 0.50 | 0.63 | 1:1 |
| Penicillium sp | 128 | 32 | 48 | 16 | 0.38 | 0.50 | 0.88 | 3:1 |
|  | 128 | 32 | 16 | 16 | 0.13 | 0.50 | 0.63 | 1:1 |

Synergistic ratios of compound A:compound B range from 3:1 to 1:3

TABLE 2

Compound A = Guazatine
Compound B = Propiconazole

| ORGANISM | QA | QB | Qa | Qb | Qa/QA | Qb/QB | SI | A:B |
|---|---|---|---|---|---|---|---|---|
| Alternaria sp. | 16 | 4 | 1 | 3 | 0.06 | 0.75 | 0.81 | 1:3 |
|  | 16 | 128 | 16 | 16 | 0.50 | 0.13 | 0.63 | 1:1 |
| Ophiostoma sp | 1 | 1 | 0.25 | 0.75 | 0.25 | 0.75 | 1.00 | 1:3 |
|  | 1 | 1 | 0.25 | 0.75 | 0.25 | 0.75 | 1.00 | 3:1 |
| Diplodia sp | 64 | 4 | 4 | 4 | 0.06 | 0.50 | 0.56 | 1:1 |
| Penicillium sp | 32 | 64 | 4 | 12 | 0.13 | 0.19 | 0.31 | 1:3 |
|  | 32 | 64 | 4 | 12 | 0.13 | 0.19 | 0.31 | 3:1 |

Synergistic ratios of compound A:compound B range from 3:1 to 1:3

TABLE 3

Compound A = Guazatine
Compound B = Iodocarb

| ORGANISM | QA | QB | Qa | Qb | Qa/QA | Qb/QB | SI | A:B |
|---|---|---|---|---|---|---|---|---|
| c versicolor | 64 | 16 | 8 | 4 | 0.13 | 0.50 | 0.63 | 1:1 |
|  | 64 | 16 | 8 | 8 | 0.13 | 0.50 | 0.63 | 1:1 |
| Penicillium sp | 128 | 4 | 4 | 4 | 0.03 | 1.00 | 1.03 | 1:1 |

Synergistic ratios of compound A:compound B are 1:1

TABLE 4

Compound A = Dodine
Compound B = Propiconazole

| ORGANISM | QA | QB | Qa | Qb | Qa/QA | Qb/QB | SI | A:B |
|---|---|---|---|---|---|---|---|---|
| C versicolor | 62.5 | 1.95 | 1.95 | 1.95 | 0.03 | 1.00 | 1.00 | 1:1 |
| Penicillium sp | 125 | 125 | 62.5 | 62.5 | 0.50 | 0.50 | 1.00 | 1:1 |

Synergistic ratios of compound A:compound B are 1:1

As can be seen by review of Tables 1–4, the compositions of the invention demonstrate synergistic microbiocidal activity as measured by minimum inhibitory concentrations (MIC) and show surprisingly greater activity than the algebraic sum of the individual components which make up each composition.

The synergistic activities of the compositions of the invention in most cases are applicable to fungi, especially wood destroying and wood staining fungi. Thus, the combinations not only lower the use level of biocide but also broaden the spectrum of activity. This is especially useful in situations where either component-alone does not achieve the best results due to weak activity against certain organisms.

What is claimed is:

1. A microbiocidal composition including synergistic effective amounts of a first component which comprises a guanidine compound selected from the group consisting of guazatine, dodine or Befran, a second component which is 3-iodo-2-propynylbutyl carbamate, wherein the weight ratio of first component to second component is in the range of from about 150:1 to about 1:250.

2. The microbiocidal composition containing from about 5 to about 30% of the composition of claim 1.

3. The microbiocidal composition of claim 2 further including an emulsifier and water.

4. The microbiocidal composition of claim 3 wherein the weight ratio of the first compound to the second compound is in the range of from about 32:1 to about 1:2.

5. The microbiocidal composition of claim 1 wherein the weight ratio of dodine, guazatine or Befran to the second component is from about 32:1 to 1:16.

6. The microbiocidal composition of claim 1, wherein said first component is guazatine and said second component is 3-iodo-2-propynylbutyl carbamate.

7. A method of inhibiting the growth of fungi, in a locus subject to contamination by fungi, which includes incorporating into or onto the locus a synergistic effective amount of the composition of claim 1.

8. The method according to claim 7 wherein the locus is an aqueous medium.

9. The method according to claim 7 further including an emulsifier and water.

10. The method according to claim 7, wherein said first component is guazatine and said second component is 3-iodo-2-propynylbutyl carbamate.

* * * * *